United States Patent [19]

Wojcienchowski et al.

[11] Patent Number: 4,802,195
[45] Date of Patent: Jan. 31, 1989

[54] DEVICE FOR METHOD FOR MANIPULATING A PART

[75] Inventors: Charles R. Wojcienchowski, West Chester; Douglas S. Steele, Fairfield, both of Ohio; Henry J. Scudder, III, Boston, Mass.

[73] Assignee: General Electric Company, Cincinnati, Ohio

[21] Appl. No.: 832,974

[22] Filed: Feb. 25, 1986

[51] Int. Cl.$^4$ .............................. G01B 15/06
[52] U.S. Cl. ........................ 378/58; 378/204; 378/208
[58] Field of Search .................. 378/58, 204, 208

[56] References Cited

U.S. PATENT DOCUMENTS

| | | | |
|---|---|---|---|
| 2,885,557 | 5/1959 | Kizaur | 378/58 |
| 3,008,049 | 11/1961 | Cherry | 378/58 |
| 3,766,387 | 10/1973 | Heffan et al. | 378/208 |
| 4,422,177 | 12/1983 | Mastronardi et al. | 378/208 |
| 4,600,998 | 7/1986 | Huet | 378/58 |

Primary Examiner—Carolyn E. Fields
Assistant Examiner—David P. Porta
Attorney, Agent, or Firm—Derek P. Lawrence; Nathan D. Herkamp

[57] ABSTRACT

A manipulator for positioning a part includes a manipulator mandrel, manipulator arms, a pneumatic actuator ball plunger, drive motors, and shaft encoders. The motors drive the manipulator mandrel vertically perpendicular to a plane of directed X-ray beams and one whose rotation axis is vertical and perpendicular to the plane of the directed X-ray beam. The motors include positioning encoders which generate encoding pulses representative of movement of the manipulator mandrel along either axis. The pneumatic ball plunger provides for the acquiring of a gripper which holds a part to be inspected in the X-ray beam. The manipulator mandrel includes two L-shaped arms inwardly extending towards the ball plunger for acquiring a gripper having outwardly extending flanges.

7 Claims, 8 Drawing Sheets

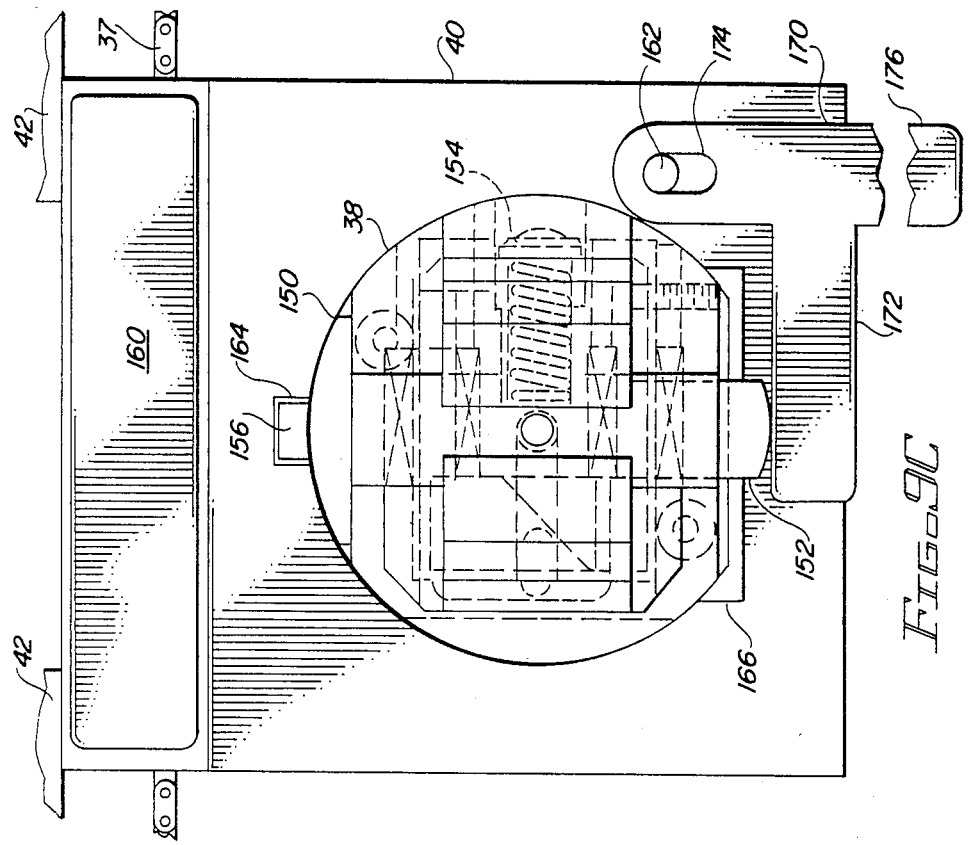
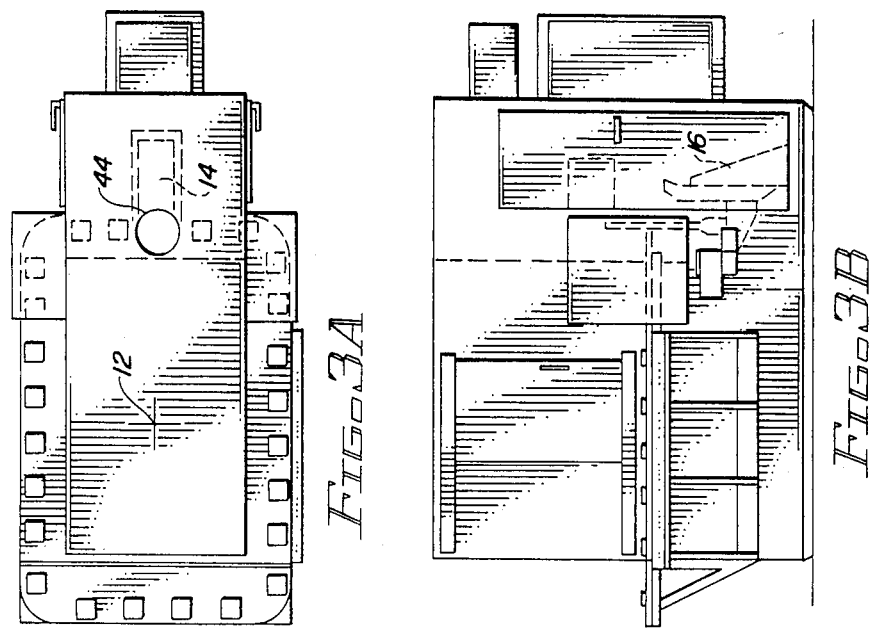

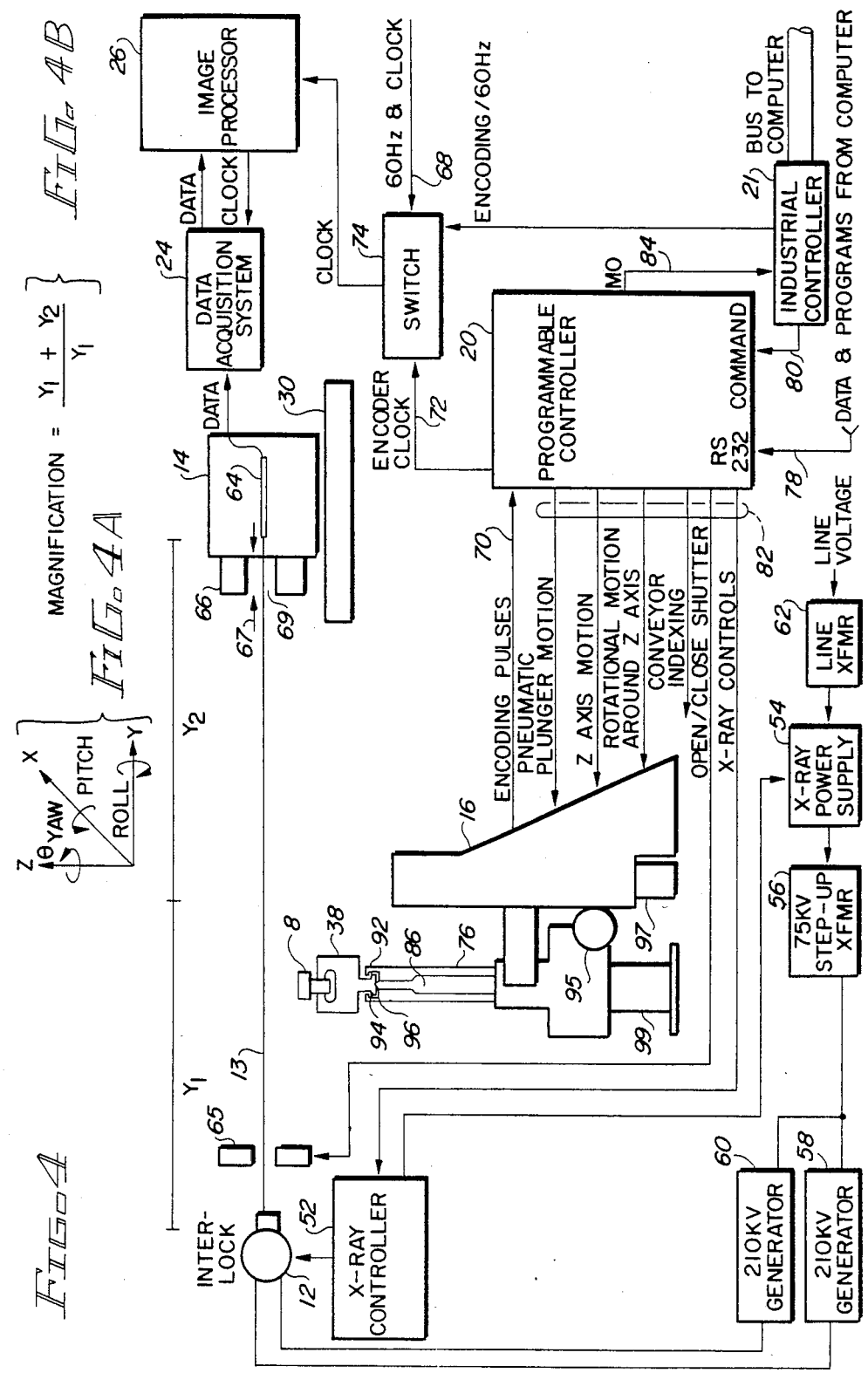

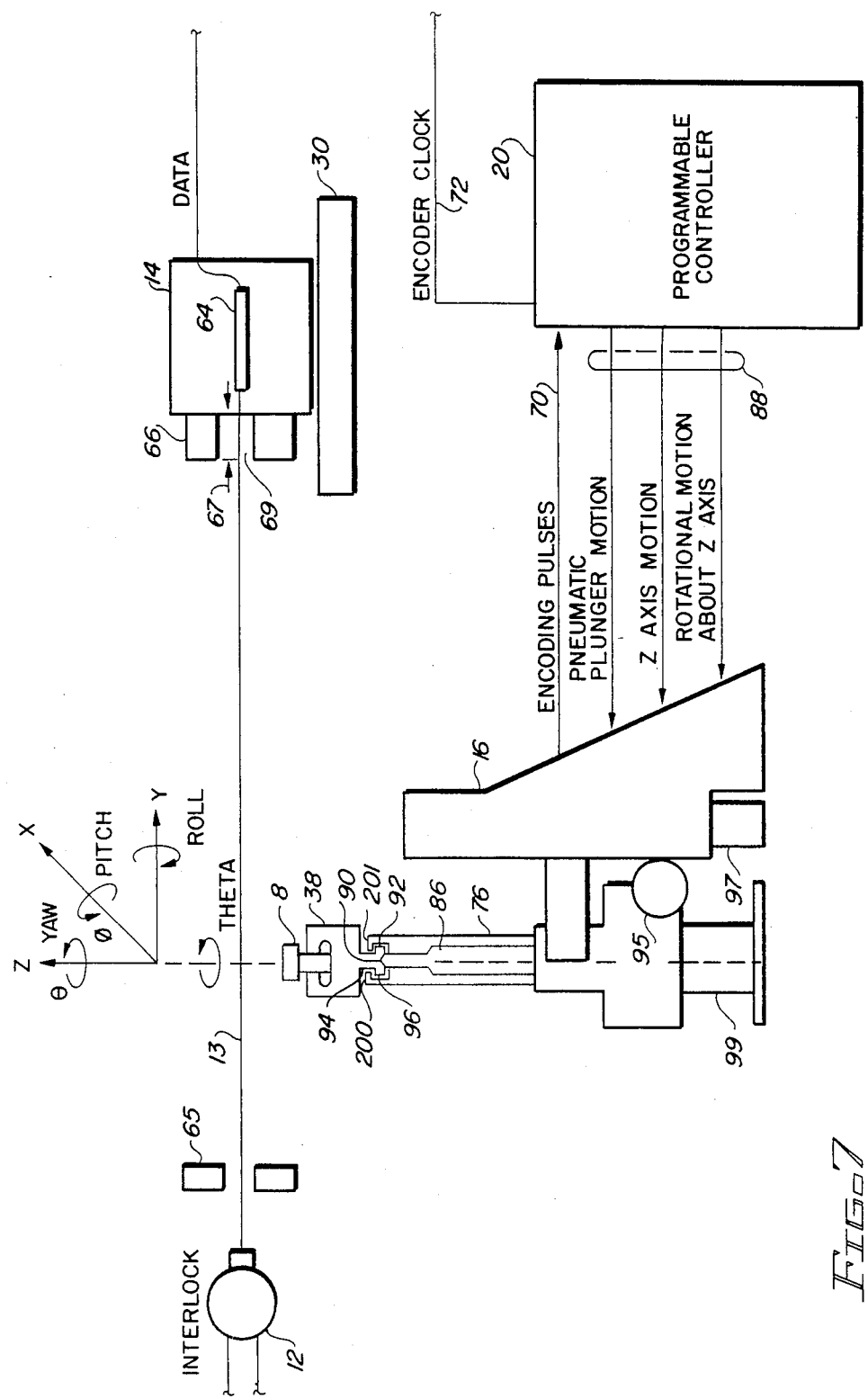

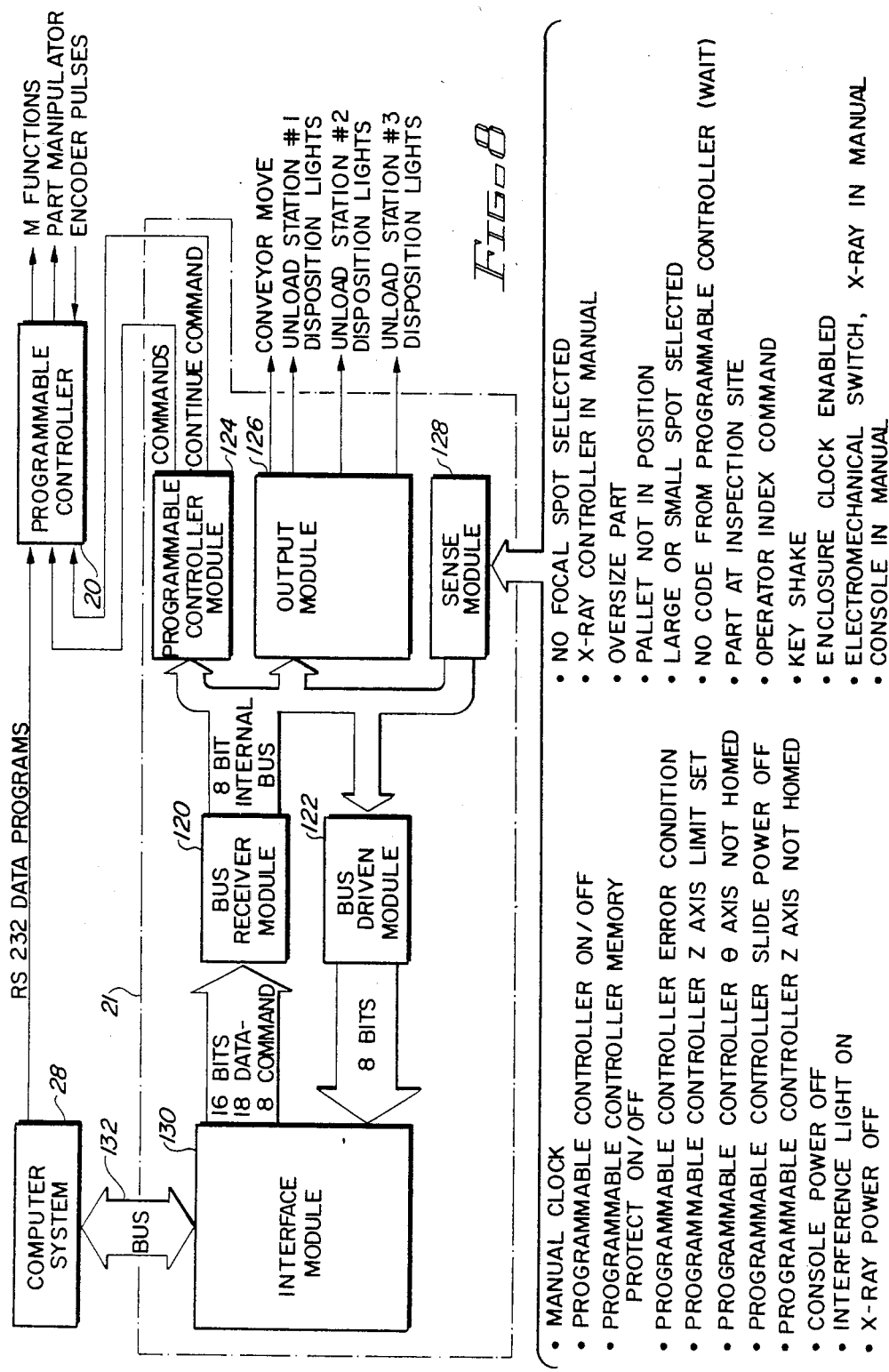

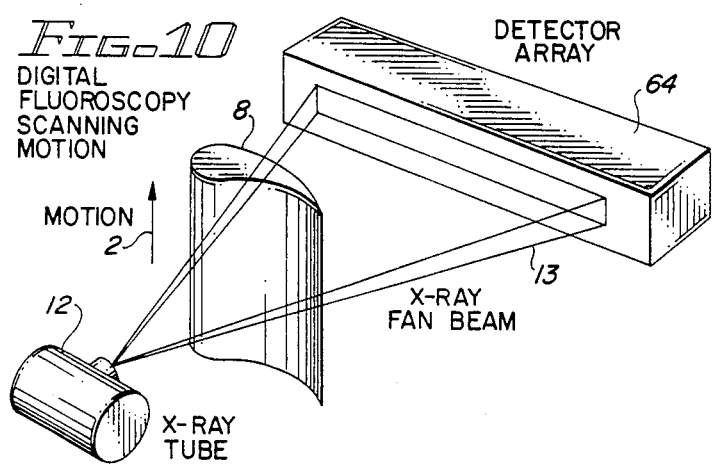
FIG-10 DIGITAL FLUOROSCOPY SCANNING MOTION
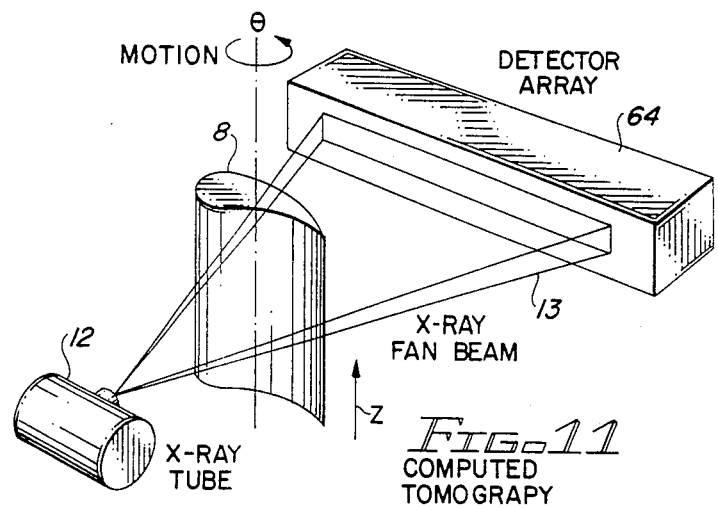
FIG-11 COMPUTED TOMOGRAPY
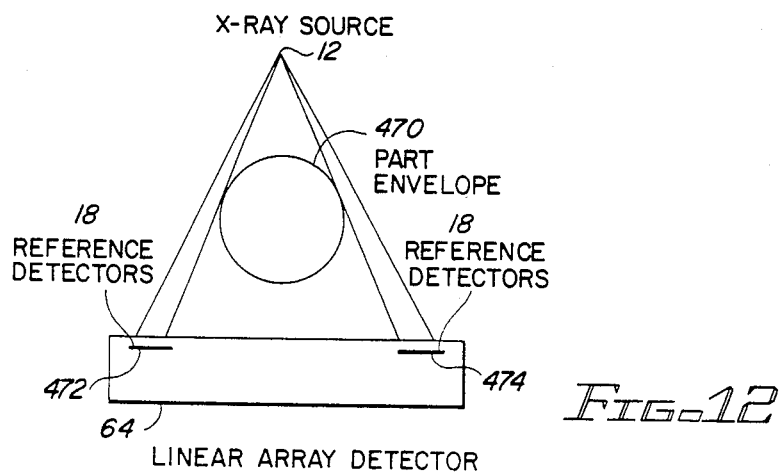
FIG-12

DEVICE FOR METHOD FOR MANIPULATING A PART

BACKGROUND OF THE INVENTION

A. Field of the Invention

This invention generally relates to manipulators of manufactured parts, and more particularly, to a manipulator for an automated digital X-ray inspection system for evaluating aircraft engine gas turbine blades.

B. Discussion

The manufacture of high performance, fuel efficient aircraft turbine engines has lead to the development of turbine blades containing complex interior passages and openings to the blade surface for blade cooling. Performance and life of the blades is dependent upon the manufacture of these interior structures within specification. A high penalty exists for blade failure because of machinery damage, incompletion of mission, and hazard to personnel. For these reasons 100% inspection of turbine blades is important to the public and a highly automated digital X-ray inspection station system has long been desired.

The automated X-ray inspection system includes an X-ray machine and an X-ray image system. The X-ray machine includes devices for manipulating parts, generating X-rays, detecting X-rays, and controlling the flow of parts through the X-ray machine. The X-ray image system includes computer hardware and software for acquiring X-ray data, image generation, archiving, displaying, performing computations, and controlling the X-ray machine. The system is a production type automatic inspection module capable of detecting internal flaws in jet engine turbine blades.

The X-ray inspection system operates as follows for a group of parts, such as turbine blades. The operator enters into the computer console information required to select as inspection plan from the computer system. The first part is then removed from an input box and the part serial number entered in the computer console. The operator then manually inserts the part into a conveyor gripper positioned at a load station. After the part is positioned the operator depresses the start buttons on the conveyor when ready. This operation is repeated for all parts. The conveyor advances the parts between load, inspection, and unload stations.

The part and gripper are automatically advanced to a part inspection station. The part grippers have variable holding configuration for accommodating a variety of parts to be inspected that are made of a material of lower X-ray absorptivity compared to the part material. When the part grippers reach the inspection station, a manipulator has to removed the part grippers from the conveyor and positions the part and grippers between an X-ray source and an X-ray detector. The manipulator moves the part within a directed x-ray beam for generating digital fluoroscopy and computed tomography images. After inspecting the blade, the manipulator replaces the gripper and part on the conveyor. The conveyor then moves the gripper and part to the unload station.

Therefore, it is an object of the present invention to provide a manipulator which controls positioning a gripper at a part inspection station.

It is an object of this invention to provide a manipulator which has two axes of movement, one axis is a vertical translation perpendicular to a directed X-ray beam, and the second is a rotation about the vertical axis.

It is an object of this invention to provide a manipulator that centers and aligns the gripper's center of axis about the vertical axis of the manipulator.

It is another object of this invention to provide a manipulator that acquires the gripper and holds the gripper firmly while positioning the gripper in the directed X-ray beam.

It is another object of this invention to provide a manipulator that provides timing pulses for data acquistion to the computer hardware based upon the motion of the gripper and part.

SUMMARY

A manipulator for positioning a part in a plurality of positions includes a manipulator mandrel, manipulator arms, a pneumatic operator ball plunger, drive motors and shaft encoders. The drive motors drive two servo controlled axes, one mounted vertically whose direction is perpendicular to a plane of directed X-ray radiation and one axis whose rotation axis is vertical and perpendicular to the plane of the directed X-ray beam. The motors have positioning encoders attached to the drive shaft of the motors which generate encoding pulses representative of movement of the manipulator mandrel in either axis. A gripper with flanges that extend outwardly from its center engage the manipulator arms. The manipulator arms extend inwardly towards the ball plunger and acquire the gripper. The gripper includes a cone shaped centering shaft which accepts the ball plunger. The ball plunger mounted in the mandrel of the manipulator is forced into the cone shaped centering shaft for retaining the gripper on the manipulator. The manipulator includes a telescoping air cylinder attached to a fixed position for offsetting the weight of the vertical axis slide mechanism and rotary axis mechanism.

BRIEF DESCRIPTION OF THE DRAWINGS

FIG. 3A-B shows a schematic diagram of the conveyor system and lead shielded chamber.

FIG. 4 illustrates the electromechanical apparatus of the X-ray machine.

FIG. 7 is a diagram of the manipulator.

FIG. 8 illustrates a detailed flow diagram of data transfer between the computer system, industrial controller and the programmable controller.

FIG. 9A-C show the gripper assembly and manipulator arms of the present invention.

FIG. 10 shows the motion for a DF image.

FIG. 11 shows the motion for a CT image.

FIG. 12 shows the configuration of the reference detectors.

GENERAL DESCRIPTION

Figure 1:
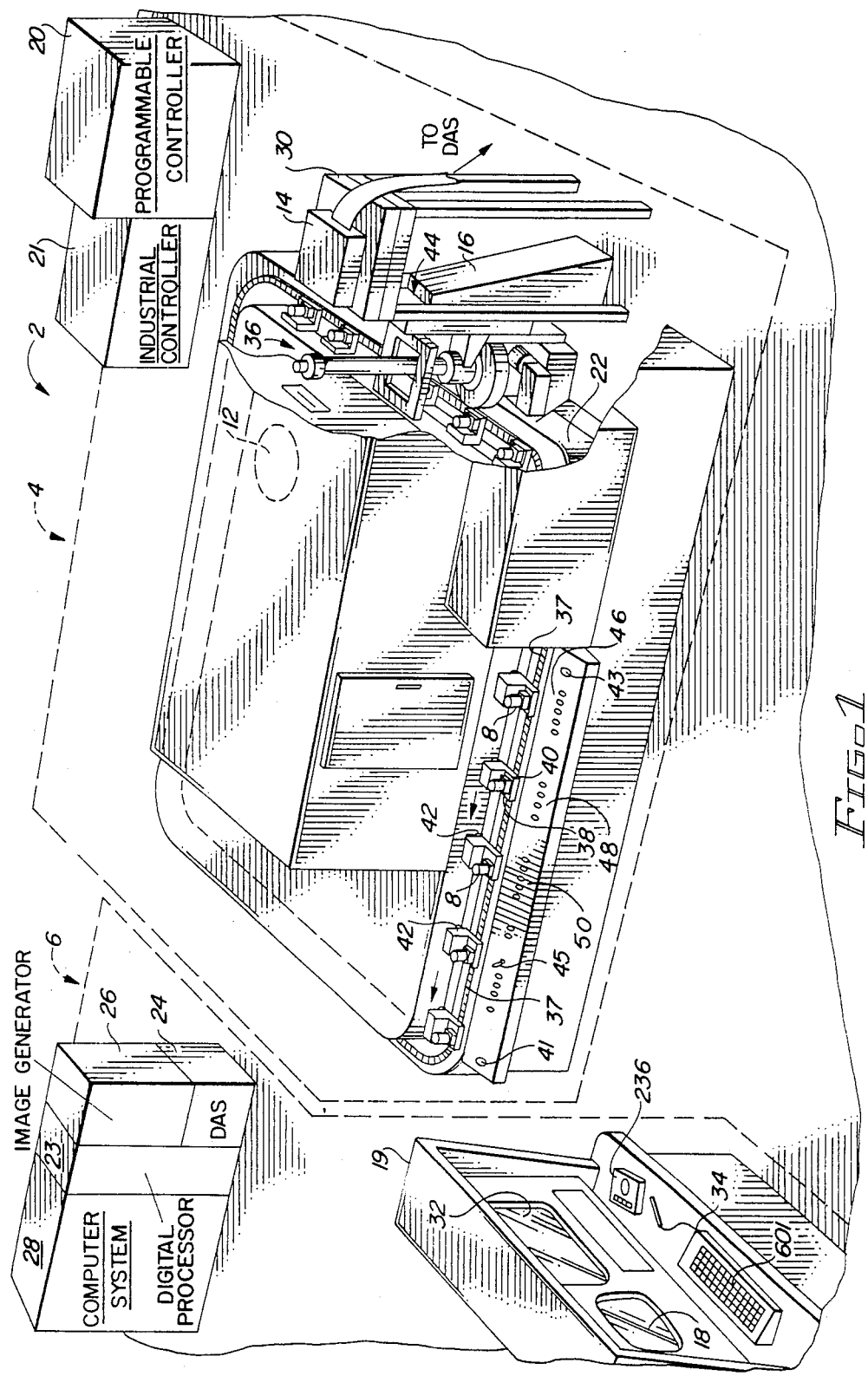
FIG. 1 illustrates the basic components of the X-ray inspection system.

FIG. 1 illustrates the basic components of the x-ray inspection system 2. The x-ray inspection system 2 includes a x-ray machine 4 and a x-ray image system 6. The x-ray machine 4 comprises a x-ray source 12, a x-ray detector 14, a part manipulator 16, a programmable controller 20, an industrial controller 21, a 6 axis movable platform 30 and a conveyor belt system 22. The x-ray image system 6 includes a data acquisition system 24, an image generation system 26, a computer system 28, an operator console 19, an operator display 18, a keyboard 601, a display processor 23, a high resolution display 32, and a bar code reader 34.

A suitable x-ray inspection system for inspecting parts with x-rays is disclosed in U.S. patent application Ser. No. 832,511 titled X-ray Inspection System, filed concurrently herewith, assigned to General Electric Company. The disclosure which is hereby incorporated by reference. While the present invention is described hereinafter with particular reference to the x-ray inspection system, it is to be understood at the outset of the description which follows that is contemplated that the device and methods in accordance with the present invention may be used with numerous manipulators for gripping various manufactured parts.

Figure 2:
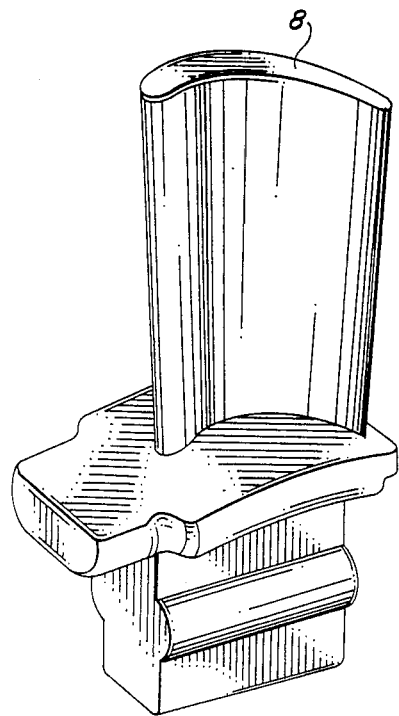
FIG. 2 is an engine turbine blade.

Parts 8, such as aircraft engine blades, are carried into the x-ray machine 4 by conveyor belt system 22. While the present invention is described hereinafter with particular reference to blades, it is to be understood at the outset of the description which follows that it contemplated that the apparatus and methods in accordance with the present invention are used to manipulate numerous other manufactured parts. These include but are not limited to various parts of turbine engines, such as compressor or turbine blades, vanes, nozzles, thermocouples, etc. FIG. 2 illustrates a typical engine blade Referring back to FIG. 1, an operator loads a blade 8 into a gripper 38 which is held to the conveyor 22 by a pallet 40 supported on the conveyor 22 system by rollers 42.

The operator informs the X-ray inspection system 2 of the part number of the blade and the type of inspection required. The operator simultaneously presses the start buttons 41 and 43. The conveyor 22 advances the blade 8 as shown in the direction of the arrow through 18 stations or positions to an inspection station 44. The inspection station 44 is inside a lead shielded chamber (shown in FIG. 2). The numerically controlled manipulator 16 removes the gripper 38 with the blade 8 from the conveyor 22 and positions it in appropriate path through a directed X-ray beam 36 between the X-ray source 12 and X-ray detector 14.

The X-ray image system 6, following an inspection blade plan, produces a digital fluoroscopy image or a computed tomography image. For digital fluoroscopy images, hereinafter referred to as DF images, the blade 8 is held at a constant angular position and moved by the manipulator 16 vertically through the X-ray beam. FIG. 10 shows the motion for a DF image. For computed tomography images, hereinafter referred to as T images, the blade 8 is held at a constant vertical position and rotated by the manipulator 16 up to 360 degrees. FIG. 11 shows the motion for a CT image. Referring back to FIG. 1, every 60th of a second the intensity of the transmitted X-rays is collected from 636 horizontal detector elements of the X-ray detector 14 by the data acquisition system 24. The collected data are feed from the data acquisition system 24 to the image generating system 26, where it is normalized for changes in X-ray tube output, channel gain, and sensitivity variations. The data is then corrected for beam hardening.

In the case of a DF image in which the blade 8 scanned vertically, the data is stored on the computer system 28. In the case of CT images, in which the part is rotated, further processing by convolution and back projection for obtaining the CT image is done in the image generator 26. The CT image is then transferred to the computer system 28 for display and storage. After all DF images and CT images are collected by the computer system 28 the manipulator 16 returns the blade 8 part to the conveyor 36. The conveyor 22 advances, and a blade 8 eventually emerges from the X-ray chamber to the first of three unload stations 46, 48 and 50. The computer system 28 analyzes the DF or CT image for identifying the location of rejectable flaws in the blade. In manual mode, the operator determines the flaw location and measures the flaws. The operator then determines the disposition of the part or if further analysis, such as a CT image is required an automatic flaw analysis process determines whether the blade is acceptable, rejectable, or requires further inspection. A flaw report is generated and lights on the unload station are activated for notifying the operator of the blade disposition.

The X-ray image system 6 controls part flow, computer task coordination, operator validation and logging, X-ray warmup and logging, blade imaging, data acquisition, flaw detection, quality control plan execution, part image archiving, part flow analysis, and part report generation. In automatic mode, the X-ray image system 6 performs automatic image analysis in real time. The image data for a blade is obtained in real time while the blade is being manipulated.

FIG. 3A-B show a schematic diagram of the conveyor 22 and the lead shielded chamber. The X-ray inspection system processes blades in a sequential fashion, dictated by the physical part conveyor 22. The throughput of the X-ray image system is limited by the scan time of the blade and the processing time of the blade. The blade scan time is a function of the physics of x-raying the blade, the data acquisition system 24, the size of the blade, and the type of scan (DF or CT). Blade processing time is a function of the size of the blade image, the processing to be applied to the image, and the number of images for the blade. The X-ray image system processes a blade during the scan time of the blade or next blade for achieving real time operation.

The X-ray inspection system operates in either manual or automatic mode. In manual the system allows the operator to make a blade image, display the image, blade disposition, and repeat if necessary. The automatic mode performs automatic flaw detection flaw analysis, and blade disposition.

X-RAY SOURCE

FIG. 4 illustrates the electromechanical apparatus of the X-ray machine 4. The X-ray source includes a X-ray control unit 52, an X-ray power supply 54, a 75KV step up transformer 56, two 210KV high tension generators 58 and 60, the X-ray tube 12 and an oil cooler (not shown). The line power is fed through the X-ray power supply 54 to the 75KV step up transformer. Each high tension generator (58 and 60) is fed from the 75KV step up transformer 56. Each high tension generator applies its potential across the tube to generate a 420KV potential. 210KV from generator 58 to the tube and 210KV from generator 60 to the tube for generating 420KV accelerating potential is a manner well known in the art.

The X-ray controller 52 regulates beam current, filament current and filament voltage. The X-ray controller 52 has safety interlocking circuitry for shutting the X-ray source 12 off if over temperature, over wattage, or X-ray machine door openings are sensed. Basically, the X-ray controller 52 controls the filament voltage and current, monitors the temperature and flow of cooling oil, shuts the system down if temperature or current exceed predetermined values, and monitors X-ray machine access door openings. The oil cooler draws the heat away from the tungsten target in the X-ray tube. The oil cooler is an oil to air heat exchanger.

A kilovoltage level for the X-ray tube is set manually or is set by the X-ray controller 52 in the X-ray power supply 54 by a D/A convertor circuit in response to commands from the programmable controller 20. For a detailed description of the function of the programmable controller attention is directed to section 7 of the disclosure. The voltage from the X-ray controller, proportional to the X-ray tube kilovoltage needed by the X-ray tube, drives a servo system in the X-ray power supply 54. The servo system drives a roller in the power supply 54 to an appropriate tap point. To achieve a constant voltage on the X-ray tube a motor drive is disabled which moves the roller in the power supply 54. The motor drive servo system is disabled while data are being taken. The servo system has a very long time constant and is underdamped. In response to changing input line voltage conditions, large overcorrection and undercorrection voltage swings occur on the input to the X-ray tube. To minimize the input line variation, a line stabilizing transformer 62 with a harmonic filter on the output is used. The line stabilizing transformer 62 minimizes voltage changes in the input to the X-ray tube. The above steps archive a constant voltage on the X-ray tubes.

Since the X-ray inspection system is developed for a factory environment, throughput is a crucial concern. In order to keep up with production rates, one DF image every 30 seconds is obtained. For an 1800 line image, this requires each line of the image to be acquired in 1/60 second. If desired, the system allows synchronization of data acquisition through the power line frequency and to minimize the effects of noise in the system. For the 420KVP X-ray tube used in this system, a reasonable signal to noise signal is achieved in 1/60 second. For better results the data from more than one data acquisition can be averaged.

X-RAY DETECTOR

A. Linear Array Detector

Referring to FIG. 4, there is also shown the scanning apparatus of the X-ray machine 4. The X-ray source 12 generates a directed X-ray beam along the Y axis through a X-ray source limiter 65 to an X-ray detector 14. The X-ray detector 14 includes a beam collimator 66 which prevents scattered radiation from impinging upon a linear array detector 64. The detector collimator 66 extends in front of the detector to eliminate as much background radiation from the X-ray source as possible. The linear array detector 64 consists of 636 individual detector elements aligned along the horizontal axis X. The detector 14 consists of an ionized chamber X-ray detector including a parallel plate capacitor with gas dielectric along with a high voltage power supply and a charge measuring device. Incident X-rays ionize the dielectric material and the ions which are formed and are swept to the collector plates under the influence of an applied electric field. The measured current is proportional to the incident X-ray flux and is relatively independent of the applied voltage over a wide range of voltages. For a more detailed description of the ionized chamber and X-ray detector array reference is made to U.S. patent application Ser. No. 565,691, titled Ionization Detector, filed Dec. 27, 1983, assigned to General Electric Company. The disclosure which is hereby incorporated by reference.

The X-ray detector consists of 600 data channels. In addition to the 600 data channels in the X-ray detector 64, 36 reference channels are provided. There are 18 reference channels on each side of the primary array and separate from it by 220 mils. The reference detectors have two major functions. The first is to take account of fluctuations in the X-ray source in intensity. In addition, the reference channels are outside the part envelope and hence have a direct air path to the source. That is the X-ray source impinges on the reference channels without passing through the blade. Any change in signal level in these channels is related to changes in source intensity. The data channels are normalized to the average value in the reference channel during each data acquisition interval. For a better understanding of the reference detectors, attention is directed to FIG. 12 which shows the configuration the reference detectors in detail. There is shown a top view of the X-ray source 12 and linear array detector 64. The area outlined generally by 470 is the area occupied by a turbine blade. A first bank of reference detectors 472 samples the X-ray level on a first side of part envelope 470. A second bank of reference detectors 474 are positioned on the opposite side of part envelope 470 for measuring the flex level of the X-ray source.

The second function of the reference detectors is to account for small differences in the data acquisition interval from cycle to cycle. With the 60 HZ power line as a reference clock 68, this effect is rather small for the most part, though in a factory environment, the power line period can vary by 10s of micro seconds from its nominal rate. Variations in the vertical step size for DF data acquisition occur if the 60 HZ clock 68 is used. This causes variable pixel sizes in the image which ca cause difficulty in interpretation. Though the effect is rather small it is sometimes preferable to assure the step size is the same for all steps (e.g. in vertical resolution measurements). The exact size of the increment is not important. It is the fact that the increment is always the same which is important. Therefore, it is useful to use a frequency reference other than the power line frequency 68. In particular, the programmable controller 20 which controls the manipulator for positioning the part moves with nearly constant velocity. An encoder pulse 70 is generated by the manipulator every time the blade is moved approximately 5 mils. The encoder pulse 70 is fed to the programmable controller 20 which generates an encoder clock signal 72 which is fed to switch 74. Switch 74 is controlled by the industrial controller 21. The switch 74 allows either the encoder clock 72 or the 60 HZ clock 68 to be applied to the image generator 26 which provides the clock signal to the data acquisition system. In the case where the clock to the data acquisition system is from the encoder clock 72, slight variations in the data acquisition time can also occur. This, of course, causes changes in the amplitude of the reference signal. These changes are accounted by normalization of the data channels in the X-ray detector with the reference detectors. Thus the reference detectors compensate for any change in signal level from the X-ray source and any changes caused by variations in either the 60 HZ clock 68 or the encoder clock 72.

In order to achieve a spatial resolution on the order of 10 mils the sampling theorem requires measurements based on 5 mil centers. Since all the data across the width of the blade are taken simultaneously by the linear array detector, this requires that the individual detector elements be spaced 5 mils centers. In order to achieve comparable resolution of the vertical resolution of DF imaging, a resolution of 10 mils with data taken in 5 mils steps is again required. Spatial resolution is achieved by beam collimator 66 which includes two tungsten blocks thick enough to attenuate the incident beam by a factor of 1000 and are spaced 11.5 mils apart in front of the ionization chamber (vertical spacing due to the geometry of the imaging system). The plates of the capacitor which form the detector are spaced apart in order to avoid X-rays directly incident on the collector plates. This spacing determines the detector voltage required to achieve the desired detector response time. Spatial resolution requirements set the spacing of the individual detector elements and the size of vertical movement increment.

The maximum blade size, sets the overall dimensions of detector 14, the required number of individual elements, and the number of steps in the vertical scan to complete a full DF image. A typical turbine blade fits in an envelope three inches wide by nine inches high. In a three inch wide detector with elements spaced every 5 mils, 600 detector elements are required. For a better understanding of the configuration of the detector array and the geometry of the X-ray source and X-ray detector described briefly above, attention is directed to FIGS. 10 and 11 of the drawings wherein the geometry for the DF image and CT image are illustrated in detail.

The detector 14 can be moved in any one direction of six axes by platform 30. The platform 30 moves in the X,Y,Z direction or rotates about any one of the axes in a manner well known in the art.

B Method of Aligning the Detector

Figure 5:
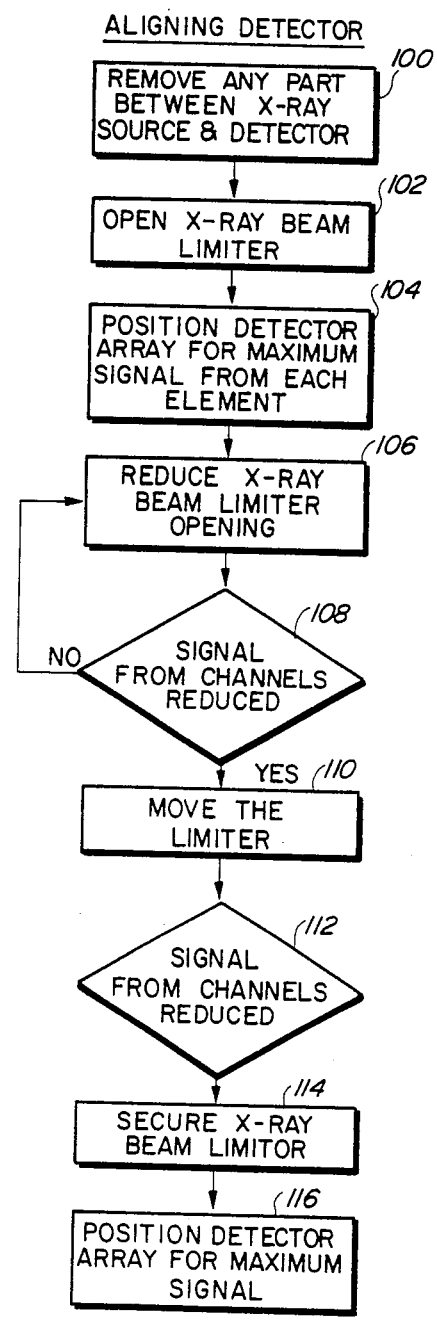
FIG. 5 is a method for aligning the detector to the x-ray source.

Before using the X-ray machine, the linear array detector 64 is aligned with the X-ray source 12. The linear array detector 64 includes 640 individual detector elements aligned along the horizontal axis X. In actual use 600 detector elements are data channels, 36 detector elements are reference channels and 4 channels are reserved. The signal from each channel is fed to the horizontal axis of an oscilloscope for displaying the intensity received by each channel from the X-ray source. The vertical axis on the oscilloscope represents the intensity. If each detector element measures the same intensity from the X-ray source, a constant level appears across the oscilloscope. The beam limiter 65 comprises two tungsten blocks separated from each other by approximately from 50 to 60 mils. A six axis platform 30 moves in the Z, X and Y direction and rotates about each axis for positioning the linear array detector 64. FIG. 5 is a flow diagram illustrating the process for aligning the X-ray detector 14.

First, an unobstructed path between the source and the detector is obtained, block 100. To begin the alignment procedure, the X-ray source beam limiter 65 is open to prevent attenuation on the detector array 64, block 102. The six axis platform 30 then positions the linear array detector 64 for maximum signal possible from each detector channel, attempting to have detector array as horizontal as is possible, block 104. When the maximum signal from each detector channel is achieved, the opening on the X-ray beam limiter is reduced by half, block 106. If the intensity of the X-ray source does not drop the width of the X-ray source beam limiter 65 is reduced until interference with the signal by limiter 65 is detected by the detector elements, block 108. The limiter 65 is then moved vertically and shifted about the X axis for achieving non-interference from the limiter 65, blocks 110 and 112. Moving the limiter 65 differentially up and down for maximum signal results in the limiter 65 centered symmetrically about the X-ray source beam. The purpose of the beam limiter 65 is to reduce the amount of extraneous radiation that strikes a blade. Reducing the amount of extraneous radiation that strikes the blade reduces the amount of scattered radiation from the blade which enters X-ray detector 14. The X-ray beam limiter 65 is then fixed in this position, block 114. Since the detector collimator 66 is securely fastened to the X-ray detector 14, the collimator 66 and detector 14 move as one unit. The depth 67 of the collimator 66 in the Y direction is approximately 750 mils. The opening 69 is approximately 12 mils. These dimensions reduce the amount of scattered radiation entering the detector 14. The depth 67 and height 69 of the collimator reduces the angle through which scattered radiation may enter the detector unattenuated. Reducing the amount of scattered radiation entering the detector 14 by increasing the height of the collimator 66 and decreasing the opening 69 produces a higher quality image than previously possible. Increasing the depth 67 and decreasing the opening 69 allows only radiation parallel to the Y axis to enter the detector. The detector 14 and collimator 66 are moved by the six axis platform 30 for producing a maximum signal, block 116. The detector array 64 and X-ray source 12 are now aligned for maximum signal.

Figure 6:
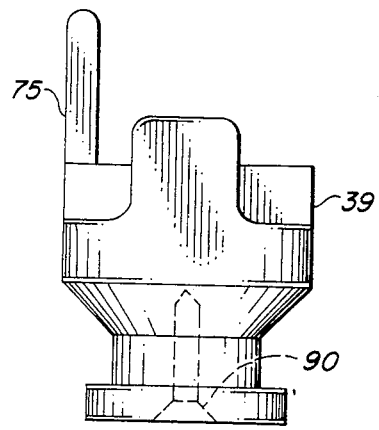
FIG. 6 is a gripper with an extension flange used for determining the center detector of the linear array detector.

One of the most crucial parts of aligning the detector is to make the center of the detector array colinear with the straight line drawn between the X-ray focal spot through the axis of rotation about the Z axis of manipulator mandrel. This function is accomplished, by rotating a gripper with an extension flange in the X-ray beam. FIG. 6 shows a gripper 39 with an extension flange 75. Referring back to FIG. 4, the center axis of rotation of the gripper 39 is the same as the center axis of rotation of the manipulator mandrel 76. The gripper 39 is securely fastened and centered on the art manipulator mandrel 76 by the plunger 86 being forced into a self-centering cavity 90. For a better understanding of the functional cooperation and components of the gripper 39 and manipulator mandrel 76 attention is directed to FIGS. 9A-C.

The oscilloscope trace is adjusted such that the data detectors span the entire oscilloscope face. The gripper 39 is held on the manipulator mandrel 76, and rotated to place the extension flange on one edge of the detector array, and moved up into the X-ray beam 13 so only the extension flange 75 intersects the beam 13 between the X-ray source 12 and the detector 14. The detector channels affected by the intersection of the flange 75 appear on the oscilloscope with a reduction in signal value compared to the majority of the other elements. From the edge of the flange 75 a first edge detector element is accurately determined from the oscilloscope. The gripper 39 is then rotated 180 degrees. A determination of a second measurement edge detector element is made. The linear array detector 64 is moved either right or left to make the first and second edge detector elements have the same relative position from each edge of the oscilloscope screen. This is checked by rotating the gripper 180 degrees, noting the position of the first edge detector, rotating the gripper 180 degrees and noting the second edge detectors position. In this iterative manner the linear array detector 64 is adjusted so the center of the detector array is nearly coincident with the axis of rotation about the Z axis of the manipulator.

A precision brass cylinder is then placed in the gripper. The brass cylinder provides a surface to measure the distance from the X-ray source focal point to the center of rotational axis of the manipulator (Y1) and the distance between the linear array detector 64 and the center of rotational axis of the part manipulator (Y2). With parameters Y1 and Y2 the magnification of the X-ray system is determined. The magnification is equal to (Y1 +Y2)/Y1. Aligning the detector prevents scattered radiation from degrading the X-ray images, provides a higher resolution image, and improves signal to noise performance.

PROGRAMMABLE CONTROLLER

FIG. 4 illustrates a basic block diagram of the operation of the programmable controller 20 in the present invention. The programmable controller 20 is a computerized numerical controller containing microcomputer which executes standard numerical control codes in a manner well known to those of ordinary skill in the art. The programmable controller 20 comprises a microcomputer (not shown), a control panel (not shown), an RS232 input port 78, a control input port 80, an encoder pulse output port 72, and M function output ports 82. The programmable controller 20 controls the position an motor drives of the part manipulator 16, through a servo control system including motor drives and shaft encoders 95 and 97. Positioning is both linear and rotary in nature. The programmable controller 20 accepts external inputs (78 and 80) and provides outputs for controlling functions on the X-ray machine. Since the programmable controller 20 is an independent processor, it is capable of being programmed to accomplish tasks. The RS232 input port 78 receives programmable controller 20 programs (or numerical code) from the computer system 28. These programs are written in programmable controller 20 code, and control, for example, the part manipulator 16 or the X-ray controller 52. The control input port 80 receives programmable controller commands from the industrial controller 24 generated by the computer system 28. The programmable controller commands emulate the front panel controls of programmable computer 20, such as enabling the programmable controller to read programs on the RS232 input port, perform a program in memory, and various other commands well known in the art. The programmable computer used by applicants n this invention is a Model SMART ICNC, manufactured by Aerotec, Inc. Accordingly, the programs written for the practice of this invention are in a language suitable for that processor. Briefly the programmable controller 20 commands are:

F Command—speed rate of the manipulator. This controls the speed of the Z axis and theta axis.

G Command—All axes home. For example, G 62 and G 63 send the Z axis and theta home separately. G 7 sends all axes home.

N Command—Loops in the programmable computer 20 code. N codes are used as sequential references for block or subroutine numbers. Certain N codes allow you to jump, repeat and access special data storage areas.

Z Command—Sends Z axis to a certain position.

D Command—Sends theta to a certain position.

M Command—Provides inputs for controlling functions.

C Command—Continues execution of the programmable computer code.

MO Command—Programmed wait for the Programmable computer 20

The MO command is used as a handshake between the programmable controller 20 and the computer 28. For example, the computer tells the programmable controller 20 to move the part manipulator mandrel 76 to a position and wait. When the programmable controller 20 executes the MO command it waits and raises a line 84 that is sensed by the industrial controller 21. The sensed condition of line 84 is sent to the computer system 28. For a better understanding of the industrial controller 21 and computer system 28, reference is made to FIG. 8 for a detailed description. When the computer system senses the wait condition of programmable controller 20 on line 84, the computer 28 issues a continue command for the programmable controller to continue. This handshaking is used when a blade is inspected. Before a blade is inspected air reference data is collected by the X-ray image system. The computer must know that the blade has been picked up by the manipulator 16 and moved into position just below the X-ray beam 13. The computer senses this through the MO line 84. The computer takes the air reference while the part is moving up to this position, and in sensing the MO knows where the blade is and then instructs the programmable computer 20 to continue.

The control of the manipulator 20 and the X-ray source 12 are accomplished by using M commands. The M commands control relays via these output lines. The relays energize various motor drives and solenoids. There are 12 output lines 82 in the programmable controller 20 controlled by M functions. Four output lines control the X-ray source kilovoltage setting. The four lines provide 16 levels of X-ray voltage from 220KV to 420KV. One output line turns the X-ray source on or off. One output line disables the motor drive on the variable X-ray power supply 54.

The servo drive motor for the variable X-ray power source is disabled to minimize any X-ray source flux variation caused by the servo system. One output line shorts a current potentiometer to provide maximum current to the X-ray source. During normal operations the X-ray source is run at maximum voltage and current. One output line enables the X-ray safety interlock circuit. One output line opens and closes the X-ray beam limiter 65. One output line activates the gripper plunger 86. One output line enables conveyor indexing.

The programmable controller 20 also generates the encoder clock pulses 72 for activating data collection from the X-ray linear array detector 64. The programmable controller 20 receives encoder pulses 70 from the manipulator 16. An encoder pulse is generated each time the Z axis moves 0.0394 mils. In a CT scan, the theta axis moves 0.00000463 degrees for every encoder pulse. The programmable computer 20 contains the necessary hardware and logic to count these encoder pulses for producing an encoder clock signal. In the illustrated embodiment, the encoder clock frequency is one timing pulse for approximately 5 mils of movement in the Z axis or 0.24 degrees in the theta direction.

Briefly, a scan subprocess in the X-ray computer system software supervises the programmable controller 20 which generates scan motion and timing pulses to the data acquisition system and image generation subsystem. Thus the programmable controller 20 and the data acquisition system are synchronized. The programmable controller 20 is commanded to home the Z axis and the rotation axis and wait. The scan subprocess senses for the completion of the homing. When the programmable controller 20 responds that the homing is complete the scan subsystem knows that the programmable controller 20 is in position to begin the scan. At this point the scan subprocess tells the programmable controller 20 to continue executing its program. At the same time the scan process changes the clock mode from the 60 HZ line reference to the encoder timing clock generated by the programmable controller 20. The scan subprocess commands the data acquisition system to begin collecting data as soon as a clock pulse is received. The number of clock pulses agrees with the number of views that the data acquisition system expects to collect. If fewer clock pulses are generated than the digital acquisition system expects, then the digital acquisition system times out and the scan stops. In this instance the X-ray computer system resets all the hardware and terminates any action on this blade. On completion of a scan, the digital acquisition system returns control to the scan subprocess as soon as the data acquisition is complete. The scan subprocess polls the programmable controller 20 to determine whether a scan is completed. Upon completion of the scan, the programmable controller responds with an appropriate command which notifies the scan subprocess that the scan is completed. The scan subprocess then issues a homing signal to the programmable controller 20. The programmable controller 20 commands the part manipulator 16 to return to a home position and release the blade and enable the conveyor. Finally, the programmable controller 20 signals the scan subsystem that the process is complete and the computer system software.

MANIPULATOR

FIG. 7 shows a diagram of the manipulator 16 used in producing DF and CT images. The manipulator includes a part manipulator mandrel 76, manipulator arms 94 and 92, a ball plunger 86, drive motors and shaft encoders 95 and 97 and a telescoping air cylinder 99. The part manipulator 16 contains the necessary hardware and logic for moving and controlling the above in accordance with the present invention in a manner well known in the art. The motors 95 and 97 drive two servo controlled axes; one mounted vertically whose direction is perpendicular to the plane of the X-rays and one whose rotation axis is vertical and perpendicular to the plane of the X-rays. The motors each have positioning encoders attached to the axis drive shaft which generate encoding pulses on line 70 when an axis is moved. The plunger 86 mounted on the rotary axis provides for the marriage of the gripper 38 o the combination of the rotary and linear axis assembly. The mandrel 76 is an aluminum assembly that includes the plunger 86. The plunger is pneumatically driven in the vertical direction in a manner well known in the art. The mandrel 76 is slotted at the top such that gripper 38 slides into the correct position above the mandrel. The top of the mandrel has two flat ground plate arms 94 and 92 into which the gripper slides. Two shoulders 200 and 201 on the arms recessed inward engage a gripper wearplate with outward flanges. The pneumatically driven plunger with a tooling ball at the top, engages the gripper 38 to the mandrel 76 by pressing the gripper ground plate 96 against the ground plate arms 94 and 92. The ball plunger is forced into a cone shaped opening which centers the gripper 38 on the mandrel 76. The manipulator 16 moves the gripper 38 with blade 8 up and down in the Z axis for a DF scan or rotates the blade 8 about the Z axis for a CT scan. The motion in the Z axis or theta direction is controlled by the programmable controller 20 through command motion lines 88 to the manipulator 16.

The telescoping air cylinder 99 provides a constant upward force on the mandrel to offset the weight of the vertical axis slide mechanism and the rotary axis mechanism. The cylinder 99 is attached below the mandrel to the ground and above to the center of mass if the rotary axis mechanism the air cylinder 99 is regulated by air pressure from an air pressure source (not shown) throughout the entire telescoping assembly as it extends upwards. The air pressure provides a vertical force to counteract the weight of the mandrel, gripper, part, rotary axis mechanism, and vertical axis slide mechanism. The air cylinder 99 prevents any torque on the mandrel allowing for better velocity control and part movement.

The manipulator 16 controls three important movements. The first movement is the movement in the Z axis. The second movement corresponds to a rotation about the Z axis. And, the third movement is the forcing of the pneumatic ball plunger 86 into a centering cone 90 in the bottom of the gripper 38. The gripper 38 on the conveyer belt is held loosely in place by a pallet 40. When the gripper 38 and pallet 40 reach the inspection station 44 the gripper 38 slides underneath and between the arms 92 and 94 of the manipulator 16. The part manipulator 16, under command from the programmable controller 20 forces the pneumatic ball plunger 86 into the centering cone 90 of the gripper 38. This action causes the gripper 38 to align directly on the Z axis with its center of rotation about the Z axis. A gripper base plate 96 is forced against the part manipulator arms 94 and 92 by the plunger 86. The force between the baseplate 96 and arms 94 and 92 firmly hold the gripper in place while the blade 8 is moved in either the Z axis or rotated about the Z axis. The blades do not have to be centered, only the gripper is centered. For CT images, as long as the blade is within approximately a 2½ inch diameter circle with the center being the center of rotation of the Z axis, an accurate CT image will be reconstructed.

Encoders 95 and 97 in the manipulator 16 generate timing pulses 70 which are fed to the programmable controller 20. The timing pulses 70 correspond to a movement in the Z axis or rotation about the Z axis. The programmable controller 20 converts the encoder pulses to a encoder clock signal to drive the data acquisition system. The data acquisition system contains an A/D convertor which converts the data from the detector array at a rate in response to the movement of the manipulator motors and passes this data to the image generator. In this manner, data is taken at exact increments in the Z direction, or rotation about the Z axis, and eliminates any synchronization problems caused by an external clock. In essence, timing signals are generated by the motion of the manipulator mandrel 76 in the Z axis or rotation about the Z axis.

INDUSTRIAL CONTROLLER

FIG. 8 illustrates a detailed flow diagram of data transfer between the computer system 28, industrial controller 21 and the programmable controller 20. System 28 communicates to the industrial controller 21 through a bus 132. The industrial controller 21 includes an interface unit 130, bus receiver module 120, bus driver module 122, programmable controller module 124, output module 126, and sense module 128. The interface unit 130 includes bus receivers and bus drivers, device address selection, decoder logic, and interrupt vector logic for transferring information between the computer system 28 and the industrial controller modules, in a manner well known in the art. The interface module may take the form of a model MDB-1710 general purpose interface unit as manufactured by MDB Systems. The interface unit 130 converts commands and data from the computer 28 to an internal bus structure 121 for bus receiver module 120. The interface unit 130 also receives data from bus 121 via bus driver module 122. The bus receiver module 120 converts 16 bit data (8 data/8 command) to an internal bus protocol for programmable controller module 124, output module 126 and sense module 128.

The programmable controller module 124 sends commands to the programmable controller 20. The commands include N commands, G commands, Z and D commands, F commands and M commands. These commands control various functions on the programmable controller. A separate line is used to send the continue command. Since the programmable controller 20 is a separate independent microcomputer, the programs for the programmable controller 20 are sent from the computer 28 via an RS232 line connected as a terminal through a terminal output board of the computer 28. For a better understanding of interface between the programmable controller, and the computer system attention is directed to FIG. 10 of the drawings.

Output module 126 controls the disposition light display on each of the unload stations. The lights correspond to dispositions of the blade when the blade reaches the unload station. The output module also controls the selection of the 60 HZ or encoder clock for generating timing pulses to the data acquisition system. In addition, the output module 126 controls conveyor movement.

The sense module 128 receives information from various sensors on the X-ray machine These sensors allow the computer 28 to detect the condition of the X-ray machine The following conditions are sensed by the sense module Programmable Controller On/Off—Checks whether the line power is switched on in the programmable controller.

Programmable Controller Memory Protect—Switch on the programmable controller which enables writing into the programmable controller memory. If it is in the protect mode, the computer 28 cannot download RS232 data into the programmable controller. The switch is located on the front panel. Programmable Controller Error Condition—Programmable controller sends a condition as to whether it has received a successful RS232 transmission from the computer 28.

Programmable Controller Z Axis Limit Set—This is an indication of extreme Z axis travel. There is a vertical upper and lower limit of travel on the Z axis, if the Z axis moved any farther, a hard crash into the end of the stationary part of the Z axis stage occurs. Optical sensors in the manipulator are detected by the programmable controller and the information is put out as a single programmable controller Z axis limit. There is no discrimination by the programmable controller between the top or bottom limit. The Z axis is homed if this error is detected.

Programmable Controller Theta Axis Not Home Monitors whether the Theta axis is homed or not. The theta axis is homed before loading for scanning a blade. At the end of a scan the manipulator mandrel is above the pallet of the conveyor belt. Z and theta are driven home before bringing the blade down and putting it on the pallet. Theta is homed first because the gripper fits correctly into the pallet only one way. An alignment pin on the gripper fits into a notch in the pallet. The Z axis home is below the surface of the pallet. Therefore, the gripper fits in the pallet correctly only when theta is homed first. If theta is not homed before moving the conveyor the next blade and gripper will not slide into the manipulator arms and will either ruin the gripper or ruin the manipulator mandrel. Thus, before scanning is indicated, or indexing can start, theta is homed to allow the gripper to slide into the top of the part manipulator mandrel. Therefore, at the end of the scan, theta is homed before the Z axis or the gripper will not fit in the pallet.

Programmable Controller Slide Power Off—Switch on programmable controller which allows the slide power to be off, but all of the electronics remain on. The slide is the Z and theta axes. The switch turns the power amplifiers off that generate the motor drive current for the axis.

Programmable Controller Z Axis Not Home—Monitors whether the Z axis is home. This ensures that the Z axis is in the proper position to allow the conveyor to index, and the next gripper and pallet to slide in without hitting (if theta is properly homed). If the manipulator mandrel is above the conveyor when indexing is initiated, damage to the mandrel or conveyor occurs.

Console Power Off—Main power switch for all the relays, relay drivers, and other circuits. It indicates whether power is applied to the electromechanical system.

Interference Light On—Conductive foam over the front of the detector is connected to a circuit that allows protection from rotations of a blade that exceeds a radius that would strike the detector. There is a three inch blade enveloped diameter. If a blade exceeds the three inches, it could strike the detector. The conductive foam covers the detector's front and when the blade strikes it, the motion of the manipulator is stopped.

X-ray Power Off—Monitors a key switch on the front of the X-ray controller that allows the power to be turned on or off.

Focal Spot Selected—Senses whether large or small focal spot is selected. A switch on the X-ray controller has three positions: large spot, no spot, and small spot. A change of the switch cannot be made from large spot to small focal spot without going through the no spot position which cuts off the X-rays. The large focal spot is used for warming up, and the small focal spot is used for images.

X-ray Controller in Manual—Senses whether the X-ray controller is in program or manual operation. Program operation is when the X-ray controller is under automatic control, setting the kilovoltage, turning the X-rays, on and disabling the servo drive. Switching to manual, allows the operator to run the X-ray machine without any need of computer interaction. It must be in program before operating the X-ray image system.

Manual Clock Control is Off—Senses a condition in which a manual clock pulse is generated. Only used for testing the system.

Pallet Not in Position—Senses whether there is a pallet in the proper position. Functionally, it is a proximity switch which senses the bolt head of one of the idle wheels on the back of the pallet. The steel mass of the bolt head makes the proximity switch change states. It detects whether the pallet has moved during an index.

Part Height Sensor—Senses if a part is to high to fit inside the X-ray chamber. If a retroreflective sensor is switched the conveyor is stopped in mid travel, with power being disabled to the conveyor drive motor.

MO—Programmable controller wait state. Senses that the programmable controller has finished moving the blade and it is waiting for a command to continue.

Part at Inspection Site—An infrared retroreflective sensor over the inspection site to determine whether a part is at the station. Keeps the X-ray system from running an inspection on a nonexistent part.

Part at Unload Site—There are three unload stations on the output side of the conveyor. An infrared retroreflective sensor senses whether a part is in the last of the three stations. If a part is at the last unload station, indexing of the conveyor is inhibited.

Operator Index Command—Senses if the conveyor push buttons have been pushed. When the operator pushes the start buttons a flip flop is set. If the conveyor switch is in automatic, the computer senses the flip flop and a conveyor move is initiated.

Keyshake—Senses a hand shaking signal from the error function in the programmable controller. When asserted this signal states that the programmable controller has disabled external command signals from the computer 28.

Encoder Clock—Senses whether the switch that controls the clock signal between the 60 HZ clock and encoder clock is switched to the encoder clock.

Large Spot—Senses if the X-ray tube is in a large spot configuration for warm-up.

Small Spot—Senses whether the X-ray tube is in a small spot configuration for imaging.

CONVEYOR

Referring briefly back to FIG. 3A-B, the conveyor 22 moves the blades through the X-ray machine. The conveyor includes chain 37, drive motors and logic hardware for indexing the blades in a manner known in the art. Operation of the conveyor in either manual or automatic mode, is via key switch 45. During computer control the conveyor operates in automatic mode. Conveyor indexing is initiated by the operator pushing the start buttons 41 and 43. The start buttons 41 and 43 are sensed by the industrial controller system 21, by setting a flip flop read by the sense module of the industrial controller 21. When the flip flop is set on, the controlling software of the computer 28 understands that the operator has pushed the buttons and wants the conveyor to index. The software, through the industrial controller 21, sends the signal to the output module for initiating conveyor advance. The conveyor moves one station. If the operator decides that he is at the end of processing a batch of blades, the operator wands in with a bar code reader, the END command. The controlling software interprets the command such that there are no more blades to be loaded onto the conveyor. When the operator pushes the buttons for the last blade advance, the system automatically advances the conveyor until the first blade that was loaded is at the inspection station. After each inspection is complete, each blade continues on, incrementally to the first unload station. There are five lights at each unload station. The lights indicate the part disposition (made either by the operator or by the automatic flaw analysis software). The disposition is classified accept, provisional accept, and dispo.

The part dispositions that correspond to the lights are:

ACCEPT—Blade has met all the criteria of the quality control inspection procedure with respect to the drawings.

PY ACCEPT—Category of provisional acceptance. The drawing has not yet been changed to reflect a new inspection criteria. Therefore, the inspection procedure itself cannot be changed. In a provisional manner while the drawing change order is in progress, work can proceed under this provisional acceptance.

DISPO—This disposition is given if the operator does not feel satisfied with his judgment about the viability of some aspect of the inspection, and the operator would like someone else to look at this image. DISPO means that the senior people will review that image and make the final disposition.

GRIPPER

Figure 9A:
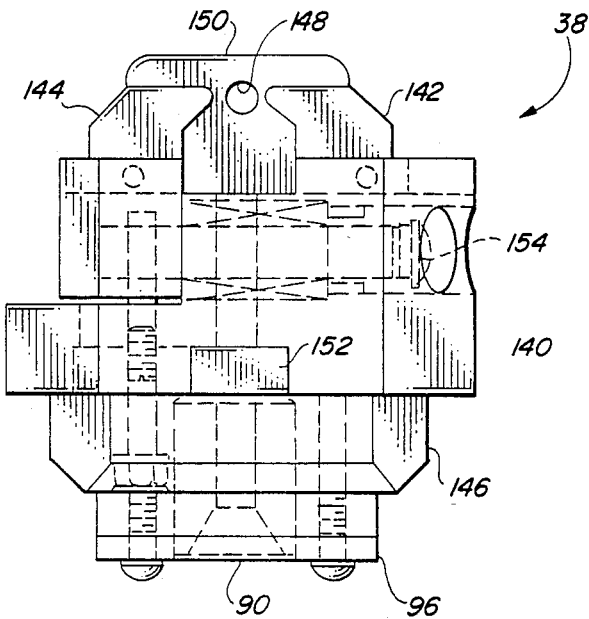
Figure 9B:
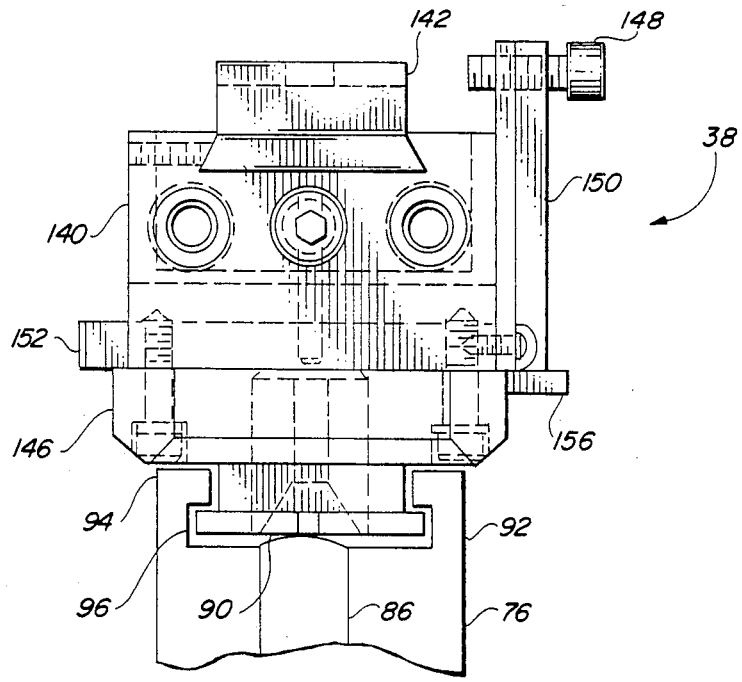

FIG. 9A-C show the gripper assembly of the present invention. FIG. 9A illustrates the front view of the gripper 38. The gripper 38 includes a gripper body 140 having a stationary jaw 142, a slidable jaw 144, a gripper base 146, a wear plate 96, an adjustment screw 148, a centering shaft 90 in the shape of a cone, an end plate 150 and a cam 152. In operation, pressing cam 152 inwards causes the slidable jaw 144 to move away from the stationary jaw 142. A blade is inserted between the jaws against the adjustment screw 148. Releasing the pressure upon cam 152 causes a spring 154 to force the slidable jaw 144 towards the stationary jaw 142 for holding the blade between the jaws. The jaws are to be made of a material whose X-ray attenuation properties are low compared to those of the part to be inspected. In doing so, the X-ray system is able to make digital fluoroscopy and computerized tomography images of the part material between the jaws, thereby allowing for whole part inspection capabilities. For a more detailed description of the gripper assembly and its operation, reference is made to U.S. patent application Ser. No. 832,982, filed concurrently herewith, titled Method and Device for Gripping Parts in an X-ray Inspection System, assigned to General Electric. The disclosure which is hereby incorporated by reference.

FIG. 9B shows a side view of the gripper inserted onto the mandrel 76 of the manipulator 16. A pneumatic control, when activated, forces the ball plunger 86 into the cone shaped centering shaft 90. The force exerted by the ball plunger 86 on the cone surface 90 forces the gripper 38 to align on its center of rotation. The center of rotation of the gripper 38 coincides with the Z axis. The force on the cone surface 90 by the ball plunger 86 causes any motion in the manipulator mandrel 76 to transfer to the gripper 38 by frictional forces exerted between the gripper wear plate 96 and the manipulator arms 94 and 92. A movement in the mandrel 76 either in the vertical direction (Z axis) or any rotational movement about the vertical axis (theta) causes a corresponding movement in the gripper 38. Essentially, the ball plunger 86 locks the gripper 38 to the manipulator mandrel while centering the gripper about the axis of rotation. An alignment pin 156 positions the gripper 38 on the conveyor pallet.

FIG. 9C shows the gripper assembly 38 inserted into the pallet 40 at the loading station 47. The pallet 40 includes a cardholder 160, a pin 162, a notch 174, an access opening 166 and rollers 42. The pallet is attached to a conveyor chain 37. The chain 37 transport the pallet 40 through the X-ray machine 4. A movement in chain 37 causes a corresponding movement in pallet 40. The chain 37 is attached to a drive motor controlled by the computer 28. The gripper 38 fits loosely into the accessing opening 166. The alignment pin 156 into the notch 164 of the pallet 40 for preventing the gripper from rotating in the pallet 40.

To assist the operator in opening the jaws a gripper tool 170 132 having an arm 172 facilitates pressing the cam 152. In operation, a gripper tool slot 174 fits over pin 162. The operator presses on a handle 176 towards the gripper 38. A pivotal action around pin 162 forces arm 172 against cam 152. The pivotal action forces cam 152 inward, forcing the jaws apart. A blade is then inserted the jaws to the end plate 150. The operator releases pressure on the gripper tool arm 176 thus releasing cam 152. In response to releasing cam 152, the jaws are forced together by a spring 154, holding the blade securely in place. The gripper tool 170 is removed. The gripper 38 with a blade securely fastened, moves through the X-ray machine on pallet 40. When the gripper 38 reaches the inspection station 44 the manipulator 16 engages the gripper 38, centers the gripper 38, locks the gripper and lifts the gripper assembly into the X-ray beam. The manipulator mandrel 76 moves through the pallet access opening 166. The manipulator mandrel 76 freely moves the gripper 38 and blade in the vertical direction and rotationally about the vertical axis for DF and CT imaging.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. A system for positioning parts in an X-ray inspection machine comprising:
   transport means for transporting parts from a part load and unload station to an inspection station in an X-ray inspection machine;
   gripper means for gripping a part and restraining the part in a predetermined orientation;
   means on said transport means for releasably carrying said gripper means;
   mandrel means in said X-ray inspection machine for removing said gripper means from said transport means and for positioning the part in said gripper means in a position for X-ray inspection, said mandrel means including:
   (i) retaining means for fixedly retaining said gripper means on said mandrel means; and
   (ii) locating means for predeterminately locating said gripper means in a preselected orientation on said mandrel means.

2. The system of claim 1 wherein said gripper means includes a cone-shaped depression formed in an external surface thereof, said locating means comprising a power driven ball-tipped plunger positioned to engage said cone-shaped depression when driven toward said gripper means, the ball-tip of said plunger being dimensioned to cooperatively mate with said depression so as to orient said gripper means in a preselected position with respect to an axis of said plunger.

3. The system of claim 1 wherein said mandrel means comprises a vertically oriented cylinder adapted for relative vertical movement about a centrally defined axis, and including drive means coupled to said mandrel means for effecting relative rotation of said mandrel means about the central axis, said retaining means being fixedly attached to the upper end of said mandrel means.

4. The system of claim 2 wherein said gripper means includes outwardly extending flanges on a base thereof and said retaining means comprises at least first and second L-shaped arms, each of said arms having inwardly oriented portions extending towards said ball-tipped plunger for engaging said outwardly extending flanges of said gripper means.

5. The system of claim 1 and including a first position sensor for sensing relative vertical displacement of said mandrel means and for providing a first output signal representative of such relative vertical displacement, a second position sensor for sensing relative rotational motion of said mandrel means and for providing a second output signal representative of such relative rotational displacement, and means responsive to said first and second output signals for positioning the part at said position for X-ray inspection.

6. A method for loading, positioning and unloading a part to be inspected by X-ray analysis in an X-ray inspection machine, the machine including transport means for mechanically transporting the part, at least one gripper operatively associated with the transport means for holding the part, mandrel means for grasping the gripper, and drive means operatively associated with the transport means and the mandrel means for selectively positioning the gripper, the method comprising the steps of:
   loading a part in a gripper with a predetermined orientation and placement with respect to the gripper;
   positioning the gripper on the part transport means;
   actuating the part transport means to move the gripper into alignment with a mandrel means in the inspection machine;
   actuating the mandrel means to grasp the gripper and remove the gripper and associated part from the transport means;
   driving the mandrel means so as to position the part in a selected location for X-ray inspection;
   actuating the mandrel means to replace the gripper on the transport means;
   operating the transport means to move the gripper to a selected location for unloading the part; and
   unloading the part from the gripper.

7. The method of claim 6 wherein the gripper includes a cone-shaped depression in at least one surface thereof, the mandrel means including a central ball-tipped plunger and an outer fixed housing, the plunger being axially movable with respect to the housing and the housing terminating in a pair of L-shaped arms having extensions directed radially inward toward said ball-tipped plunger, the gripper having flanges extending outwardly with respect to the cone-shaped depression, the steps of actuating the part transport means and the mandrel means including the further steps of:

moving the gripper such that the inwardly extending L-shaped arm extensions overlay the outwardly extending flanges of the gripper; and energizing the ball-tipped plunger so that the ball-tip is driven into the cone-shaped depression to axially center the gripper on the mandrel means.

* * * * *

UNITED STATES PATENT AND TRADEMARK OFFICE
CERTIFICATE OF CORRECTION

PATENT NO. : 4,802,195
DATED : January 31, 1989
INVENTOR(S) : Charles R. Wojciechowski, et al.

It is certified that error appears in the above-identified patent and that said Letters Patent is hereby corrected as shown below:

Inventor's name misspelled:

Charles R. Wojcienchowski should read:

--     Charles R. Wojciechowski   --.

Signed and Sealed this

Twenty-fourth Day of October, 1989

*Attest:*

DONALD J. QUIGG

*Attesting Officer*      *Commissioner of Patents and Trademarks*